United States Patent [19]

Young et al.

[11] Patent Number: 5,554,137
[45] Date of Patent: Sep. 10, 1996

[54] TISSUE PIERCING MEMBERS

[75] Inventors: Wayne P. Young, Brewster, N.Y.;
Salvatore Castro, Seymour, Conn.

[73] Assignee: United States Surgical Corporation, Norwalk, Conn.

[21] Appl. No.: 134,354

[22] Filed: Oct. 8, 1993

[51] Int. Cl.[6] .......................... A61M 5/18; A61B 17/32; B26B 5/00
[52] U.S. Cl. ........................... 604/264; 606/167; 30/336
[58] Field of Search ................... 30/152, 162, 346, 30/335, 360, 349, 358, 366, 339, 337, 329; 604/274, 272, 174, 170, 165, 164; 606/185, 184, 166–167, 170–172; 401/117, 91; D24/147

[56] References Cited

U.S. PATENT DOCUMENTS

| | | | |
|---|---|---|---|
| 1,380,447 | 6/1921 | Westcott | 452/69 |
| 3,584,624 | 6/1971 | de Clutiis | 604/170 |
| 3,995,860 | 12/1976 | Manspeaker | 30/339 X |
| 4,349,202 | 9/1982 | Scott | 30/337 X |
| 4,408,369 | 10/1983 | Scholl | 30/339 X |
| 4,414,974 | 11/1983 | Dotson et al. | 606/167 |
| 4,499,898 | 2/1985 | Knepshield et al. | 606/166 |
| 4,570,941 | 2/1986 | Saunders | 30/337 X |
| 4,601,710 | 7/1986 | Moll | 604/165 |
| 4,654,030 | 3/1987 | Moll et al. | 604/165 |
| 4,660,287 | 4/1987 | Decker | 30/339 |
| 4,723,545 | 2/1988 | Nixon et al. | |
| 5,066,288 | 11/1991 | Deniega et al. | |
| 5,116,353 | 5/1992 | Green | 606/184 |
| 5,168,630 | 12/1992 | Weber | 30/337 X |
| 5,232,440 | 8/1993 | Wilk | 604/49 |
| 5,314,417 | 5/1994 | Stephens et al. | |
| 5,342,382 | 8/1994 | Brinkerhoff et al. | |
| 5,364,372 | 11/1994 | Danks et al. | |
| 5,366,445 | 11/1994 | Haber et al. | |
| 5,385,572 | 1/1995 | Nobles | 606/185 |

FOREIGN PATENT DOCUMENTS

| | | |
|---|---|---|
| 0479565 | 4/1992 | European Pat. Off. . |
| 0604197 | 6/1994 | European Pat. Off. . |
| 4020956 | 1/1991 | Germany . |
| 921554 | 4/1982 | U.S.S.R. . |
| 1356386 | 6/1974 | United Kingdom . |
| 2063140 | 6/1981 | United Kingdom ..... 30/339 |

*Primary Examiner*—Stephen C. Pellegrino
*Assistant Examiner*—Nancy Mulcare

[57] ABSTRACT

A piercing tip for penetrating body tissue is provided which includes a conical body and a triangular cutting blade positioned within a slot formed in the conical body. The piercing tip is particularly adapted for mounting at the distal end of an obturator and for use as part of a trocar assembly.

12 Claims, 3 Drawing Sheets

TISSUE PIERCING MEMBERS

BACKGROUND OF THE INVENTION

1. Technical Field

The present invention relates to tissue piercing members and to trocar assemblies which incorporate such tissue piercing members.

2. Description of the Related Art

Trocar assemblies are well known devices for piercing body walls so as to gain access to underlying structures. In the context of minimally invasive surgical and diagnostic procedures, e.g., laparoscopic, thoracoscopic and arthroscopic procedures, the trocar is utilized to facilitate introduction of a cannula or guide sleeve through the body wall. The cannula, once positioned, provides a port of entry for additional instrumentation, e.g., an endoscope, clip applier, scissors, graspers, retractors, and the like. Recently, the development of essential mechanical instrumentation for use through cannulae has enabled the widespread acceptance of numerous minimally invasive procedures.

In introducing the initial trocar/cannula assembly through the body wall, the surgeon generally has no visualization of the body cavity or the location of internal structures. To provide an increased margin of safety, trocars have been developed which provide mechanisms adapted to cover the piercing member upon entry into the body cavity, e.g., SU 921554 to Markelov, U.S. Pat. No. 4,601,710 to Moll et al. and U.S. Pat. No. 5,116,353 to Green.

In utilizing trocar/cannula assemblies, the surgeon's control during entry is at least in part predicated on the penetration force required to pass the trocar through the body wall. The lower the force required, the more control the surgeon will have during entry. Thus, for example, U.S. Pat. No. 4,654,030 to Moll et al. provides a safety shielded trocar in which the safety shield is designed to minimize the trocar's penetration force. A variety of trocar piercing tip designs have also been disclosed, e.g., pyramidal and conical tips. U.S. Pat. No. 1,380,447 to Westcott discloses a trocar which includes a perforator or blade having a sharp tapered point and two sharp cutting edges. See also U.S. Pat. No. 4,499,898 to Knepshield et al. (surgical knife with controllably extendable blade), U.S. Pat. No. 3,584,624 to de Clutiis (catheter which receives rigid stylet with a cutting edge), U.S. Pat. No. 4,414,974 to Dotson et al. (microsurgical knife), U.S. Pat. No. 5,232,440 to Wilk (assembly for draining abscesses) and U.K. 1,356,386 to Moss et al. (artery entry tool). The design of the trocar's piercing tip will also influence the degree to which tissue is traumatized during trocar entry.

A need thus exists for a piercing tip design which maximizes the surgeon's control during trocar entry by reducing penetration force and which minimizes tissue trauma.

SUMMARY OF THE INVENTION

According to the present invention, a piercing tip is provided which is particularly adapted for use with trocar assemblies. The piercing tip minimizes penetration force and tissue trauma and is economical in manufacture, reducing the manufacturing cost of trocar assemblies relative to prior art trocar piercing tip designs.

More particularly, the piercing tip of the invention includes a conical body which defines an outer face and a base of circular cross-section. The piercing tip also includes a substantially planar cutting blade having a triangular cutting region. The cutting blade is positioned within a slot formed in the conical body such that the triangular cutting region extends at least in part beyond the outer face of the conical body. In a preferred embodiment, the conical body includes a cylindrical extension which projects from the circular base and an outwardly extending projection which is adapted to mount the conical body to an obturator. In a further preferred embodiment, the conical body is formed from first and second body portions and the slot is formed in a region intermediate these two body portions.

The invention also provides a trocar which includes an obturator defining a longitudinal axis, and a conical piercing tip body mounted to the obturator. The conical piercing tip body defines an outer face and a base of circular cross-section which is transverse to the obturator's longitudinal axis. The trocar also includes a substantially planar cutting blade having a triangular cutting region. The cutting blade is positioned within a slot formed in the conical body such that the triangular cutting region extends at least in part beyond the outer face of the conical body.

BRIEF DESCRIPTION OF THE DRAWINGS

The features and advantages of the present invention will become apparent from consideration of the following specification when taken in conjunction with the accompanying drawings in which.

DETAILED DESCRIPTION OF THE INVENTION

Figure 1:
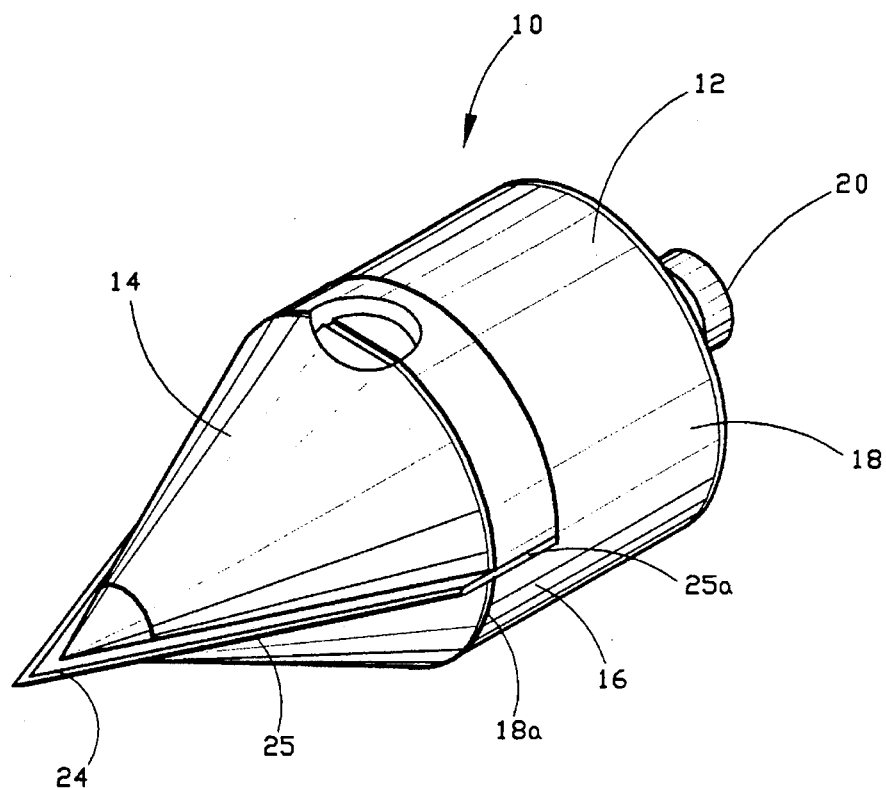
FIG. 1 is a perspective side view of a piercing tip according to the present invention.
Figure 2:
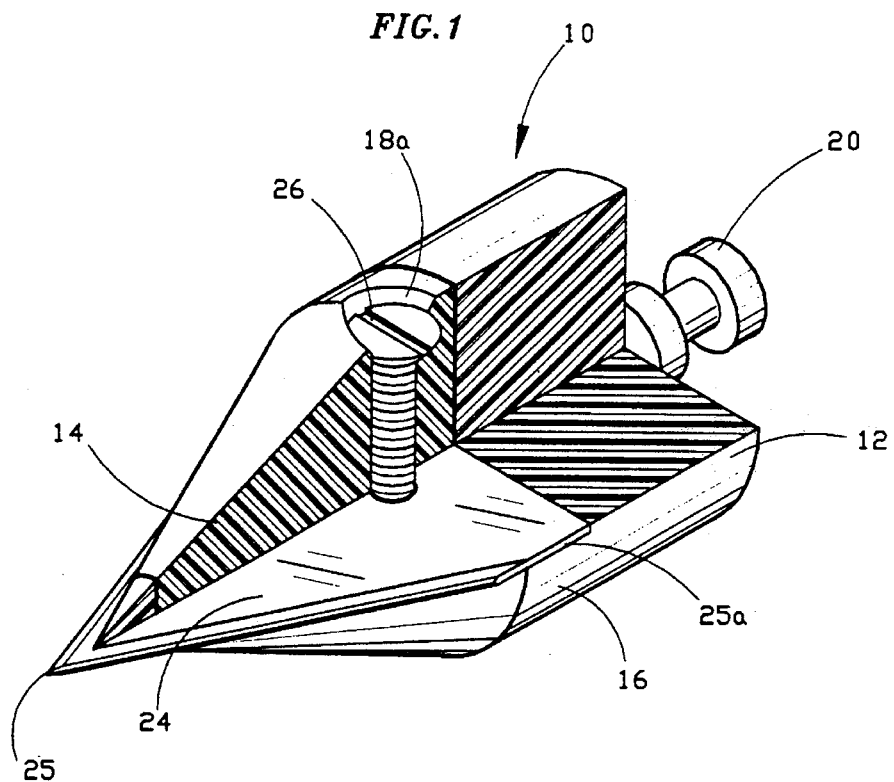
FIG. 2 is a perspective side view, partially in section, of the piercing tip of FIG. 1.
Figure 3:
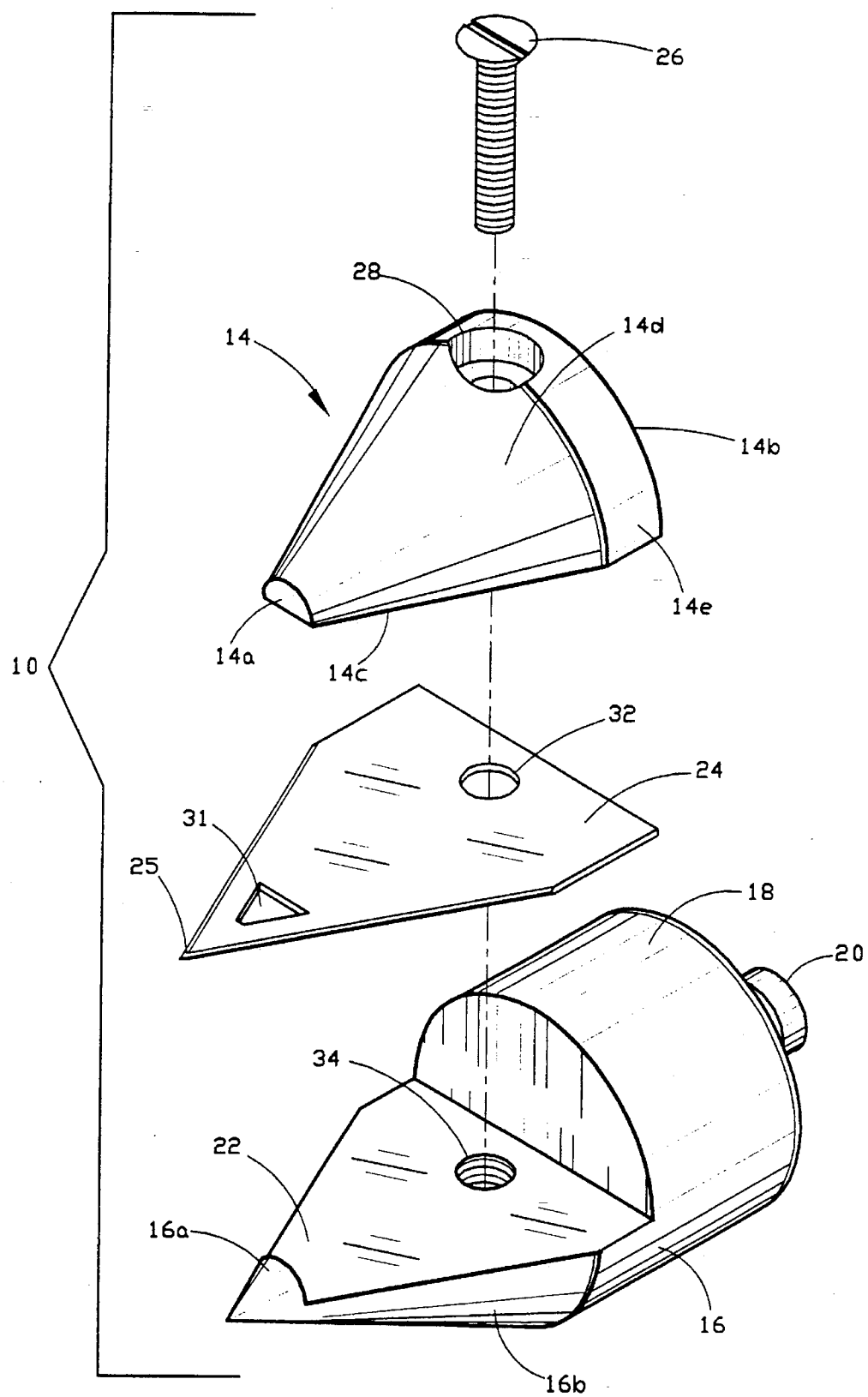
FIG. 3 is an exploded perspective view, with parts separated, of the piercing tip.

Referring to FIGS. 1–3, piercing tip 10 includes a body 12 which is formed by two body portions 14, 16. Body portion 14 defines a distal face 14a, a proximal face 14b, a planar side wall 14c, a non-planar side wall 14d having a longitudinal cross-sectional dimension that varies axially therealong and a curved portion 14e preferably having a uniform cross-sectional dimension axially therealong. Body portion 16 defines a distal conical portion 16a, an intermediate partial frustoconical portion 16b and a proximal cylindrical extension 18. Body portion 14 is adapted to cooperate with and receive the intermediate partial frustoconical portion 16b of body portion 16 such that when body portions 14 and 16 are assembled, as shown in FIG. 1, body 12 is conically configured at its distal end and includes cylindrical extension 18 at its proximal end. An outwardly extending projection 20 extends proximally from cylindrical extension 18 and is adapted to be mounted to an obturator 31 (FIG. 5).

Figure 4:
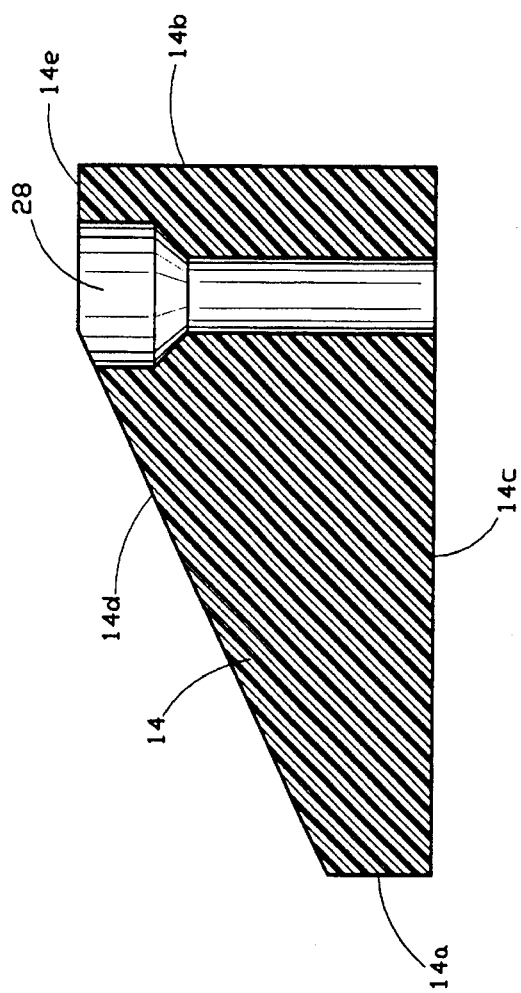
FIG. 4 is a sectional side view of a first body portion of the present invention.

A slot 22 is formed between body portions 14, 16 within which is mounted a substantially planar cutting blade 24. Slot 22 is transverse to the base 18a of cylindrical extension 18 and generally passes through the vertex defined by conical body 12. Cutting blade 24 includes a triangular distal portion and a substantially rectangular proximal portion. An aperture 31 is formed in the triangular distal portion of cutting blade 24 to receive the distal conical portion 16a of body portion 16. A screw 26 is passed through aperture 28 formed in body portion 14 (see FIG. 4), aperture 32 formed in cutting blade 24 and into aperture 34 formed in body portion 16 to secure cutting blade 24 to body 12. Of course, alternative means may be used to secure cutting blade 24 to body 12, as for example a dowel or pin. An adhesive may also be employed, either as a sole means of securement or in combination with other securement means. It is also contemplated that one or more molded keys or protrusions may be formed in body portion(s) 14 and/or 16 which may cooperate with apertures formed in cutting blade 24 to align and secure cutting blade thereto.

Figure 5:
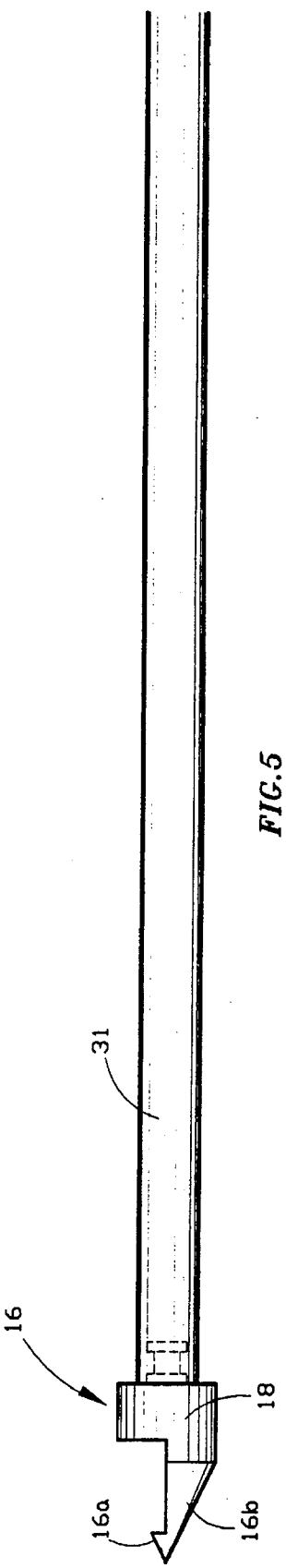
FIG. 5 is a side view of a piercing tip of the invention mounted to an obturator.

As shown in FIG. 5, piercing tip 10 is typically mounted to an obturator 31. The obturator 31 is adapted to be received in a cannula for introduction into a body cavity. Additional structures may be included as part of the trocar assembly, as is well known in the art, e.g. a valve mechanism, a desufflation lever, obturator and cannula housings, and the like. See, e.g., U.S. Pat. No. 5,116,353 to Green and U.S. Pat. No. 4,6601,710 to Moll, the contents of which are hereby incorporated by reference.

Cutting blade 24 projects beyond body portion 12 to provide an exposed triangular cutting edge 25 which incises the body wall and cuts through the tissue layers therebelow. Preferably, the triangular cutting edge 25 defines an isosceles triangle. Body portion 12 follows therebehind, dilating the body wall and tissue layers so as to facilitate introduction of the cannula. In a preferred embodiment, side face 25a of cutting edge 25 substantially aligns with the outer edge of cylindrical extension 18. By aligning side face 25a of cutting edge 25 with cylindrical extension 18, the degree to which the body wall and underlying tissue layers are cut is limited to the diameter of cylindrical projection 18. It is further contemplated that side face 25a may be recessed within cylindrical extension 18, thereby relying on the dilative function of the conically configured body portions 14, 16 to expand the incision to accommodate passage of the cannula into the body cavity.

Body portions 14, 16 are typically molded from a suitable polymer, e.g., Lexan, ABS or the like. Cutting blade 24 is fabricated from a material which will maintain a cutting edge, e.g., stainless steel.

Projection 20 is typically mounted in a cooperating socket formed at a distal end of an obturator 31. Preferably, projection 20 is adapted to rotate within the obturator socket, thereby permitting piercing tip 10 to rotate with respect to the obturator 31. Such relative motion helps to reduce tissue trauma as the piercing tip 10 is introduced through the body wall because, as the surgeon applies force to the trocar assembly, there is a tendency to rotate one's wrist. Inasmuch as the piercing tip 10 is able to rotate with respect to the obturator, the piercing tip 10 remains rotationally fixed with respect to the body wall once the body wall engages and surrounds the piercing tip 10 during entry therethrough, thereby ensuring a relatively direct entry of the piercing tip 10 through the body wall.

While the invention has been particularly shown and described with reference to the preferred embodiments, it will be understood by those skilled in the art that various modifications and changes in form and detail may be made therein without departing from the scope and spirit of the invention.

We claim:

1. A piercing tip for use in piercing body tissue comprising:

(a) a body member defining an outer face and a base portion, the body member including a first body portion defining a distal face, a proximal face, a planar side wall and a frustoconically curved side wall and a second body portion defining a distal conical portion; and (b) a substantially planar cutting blade having a triangular cutting region, the cutting blade being positioned within a slot formed in the body such that the triangular cutting region extends at least in part beyond the outer face of the body.

2. The piercing tip of claim 1, wherein the slot is transverse to the base of the body.

3. The piercing tip of claim 1, wherein the body defines a vertex and the slot is in a plane which transects the vertex.

4. The piercing tip of claim 1, wherein the body includes a cylindrical position which extends from the circular base.

5. The piercing tip of claim 4, wherein the cylindrical portion includes an outwardly extending projection which is adapted to be mounted to an obturator.

6. The piercing tip of claim 5, wherein the outwardly extending projection is adapted to be rotatably mounted to the obturator.

7. The piercing tip of claim 1 wherein planar cutting blade defines an aperture which is adapted to receive the distal conical portion therethrough.

8. The piercing tip of claim 1, further comprising an attachment member configured and dimensioned to secure the cutting blade to the body.

9. The piercing tip of claim 8, wherein the attachment member is selected from the group of a screw, dowel, pin, molded protrusion, adhesive, and combinations thereof.

10. The piercing tip of claim 1, wherein the triangular cutting region of the planar cutting blade defines a base and wherein a substantially rectangular region extends from the base.

11. The piercing tip of claim 10, wherein the width of the rectangular region is no greater than the diameter of the circular base of the cutting body.

12. The piercing tip of claim 1, wherein the triangular cutting region defines an isosceles triangle and wherein the side walls of the isosceles triangle are substantially parallel to the outer face of the conical body.

\* \* \* \* \*